United States Patent [19]

Crawley

[11] 4,307,111
[45] Dec. 22, 1981

[54] 1-HYDROCARBYLOXYPHENYL-1,2-DIPHENYLALKENE DERIVATIVES

[75] Inventor: Graham C. Crawley, Macclesfield, England

[73] Assignee: Imperial Chemical Industries Limited, London, England

[21] Appl. No.: 145,504

[22] Filed: Apr. 29, 1980

[30] Foreign Application Priority Data

May 15, 1979 [GB] United Kingdom ............... 16860/79

[51] Int. Cl.$^3$ ..................... C07C 43/215; A01N 31/14
[52] U.S. Cl. ................................ 424/278; 260/348.63; 424/340; 424/341; 568/585; 568/586; 568/640; 568/641; 568/52
[58] Field of Search ............... 568/585, 586, 640, 641; 260/348.63; 424/340, 341, 278

[56] References Cited

U.S. PATENT DOCUMENTS

| | | | |
|---|---|---|---|
| 2,301,260 | 11/1942 | Davies et al. ...................... | 568/640 |
| 2,346,049 | 4/1944 | Rohrmann ...................... | 568/640 X |
| 3,320,271 | 5/1967 | Lednicer . | |
| 3,712,929 | 1/1973 | Middleton ........................... | 568/641 |
| 3,875,242 | 4/1975 | Lednicer . | |
| 3,947,520 | 3/1976 | Lednicer . | |

FOREIGN PATENT DOCUMENTS

| | | | |
|---|---|---|---|
| 567807 | 3/1945 | United Kingdom ................ | 568/640 |
| 586493 | 3/1947 | United Kingdom ................ | 568/641 |

OTHER PUBLICATIONS

Palopoli et al., Jour. of Medicinal Chemistry (1974), 17, 1333-1335.

Richardson, Biochemical Society Transactions (1973), 528-535.

*Primary Examiner*—Bernard Helfin
*Attorney, Agent, or Firm*—Cushman, Darby & Cushman

[57] ABSTRACT

Triphenylalkene derivatives of the formula:

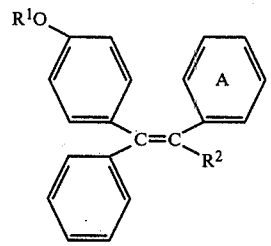

wherein $R^1$ is alkenyl, cycloalkenyl, cycloalkenylalkyl, halogenoalkenyl, hydroxyalkyl, dihydroxyalkyl, hydroxycycloalkyl, dihydroxycycloalkyl, hydroxycycloalkylalkyl, epoxyalkyl, alkoxyalkyl or alkylthioalkyl each of up to 10 carbon atoms, wherein $R^2$ is alkyl of up to 6 carbon atoms, halogen or nitro and wherein ring A may optionally bear a halogen substituent or an alkoxy substituent of up to 4 carbon atoms. These compounds possess antioestrogenic activity and are useful in the treatment of anovulatory infertility and of breast tumours. Representative of the compounds is 1-p-allyloxyphenyl-trans-1,2-diphenylbut-2-ene. There are also disclosed processes for the manufacture of the compounds and pharmaceutical compositions containing them.

7 Claims, No Drawings

1-HYDROCARBYLOXYPHENYL-1,2-DIPHENYLALKENE DERIVATIVES

This invention relates to triphenylalkene derivatives which possess antioestrogenic activity.

Many triphenylalkene derivatives are known which possess antioestrogenic activity, and these mostly have an aminoalkoxy group attached to one of the phenyl groups of the triphenylalkene structure. The most widely used such antioestrogen is tamoxifen; other similar ones are nafoxidine and clomiphene. It is also known from the Journal of Medicinal Chemistry, 1966, 9, 172 and 1969, 12, 881, that certain compounds related to nafoxidine but with the aminoalkoxy group replaced by a glyceryl group possess antioestrogenic activity. These compounds are stated to be "as a rule less potent angents".

We have now found that replacement of the aminoalkoxy group in tamoxifen by a series of non-basic groups leads to compounds the most potent of which are substantially more active than tamoxifen.

According to the invention there is provided a triphenylalkene derivative of the formula:

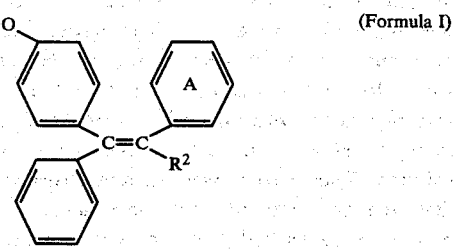

(Formula I)

wherein $R^1$ is alkenyl, cycloalkenyl, cycloalkenylalkyl, halogenoalkenyl, hydroxyalkyl, dihydroxyalkyl, hydroxycycloalkyl, dihydroxycycloalkyl, hydroxycycloalkyl-alkyl, epoxyalkyl, alkoxyalkyl or alkylthioalkyl each of up to 10 carbon atoms, wherein $R^2$ is alkyl of up to 6 carbon atoms, halogen or nitro and wherein ring A may optionally bear a halogen substituent or an alkoxy substituent of up to 4 carbon atoms.

It is clear that compounds of the formula (I) stated above can exist in the form of a cis- or a trans- isomer, in which the designation cis- and trans- refers to the relative positions of the two unsubstituted phenyl groups about the double bond. This invention is addressed to both cis- and trans-isomers and to mixtures thereof, but it is to be understood that the trans-isomer is usually preferred.

$R^1$ may be, for example, allyl, but-2-enyl, 3-methylbut-2-enyl, but-3-enyl, 1-methylprop-2-enyl, cyclohex-2-enyl, 2-chloroprop-2-enyl, 2-hydroxyethyl, 2-hydroxypropyl, 2,3-dihydroxypropyl, 1-methyl-2,3-dihydroxypropyl, 2,3-dihydroxybutyl, 3-methyl-2,3-dihydroxybutyl, 3,4-dihydroxybutyl, 2-hydroxycyclohexyl, 2,3-dihydroxycyclohexyl, 2,3-dihydroxycyclohexyl, 2,3-epoxypropyl, 2,3-epoxybutyl, 3,4-epoxybutyl, 2-methyoxyethyl or 2-methylthioethyl.

$R^2$ may be, for example, methyl, ethyl, n-propyl, n-butyl, chloro, bromo or nitro.

The optional substituent in ring A may be, for example, a chloro or methoxy substituent.

A preferred triphenylalkene derivative of the invention has the formula given above in the transconfiguration wherein $R^1$ is alkenyl, dihydroxyalkyl or epoxyalkyl each of 3 or 4 carbon atoms, wherein $R^2$ is alkyl of up to 6 carbon atoms, especially ethyl, and wherein ring A bears no further substituent.

Particular compounds of the invention are hereinafter set out in the Examples, and preferred compounds are 1-p-allyloxyphenyl-trans-1,2-diphenylbut-1-ene, 1-p-(2,3-dihydroxypropoxy)phenyl-trans-1,2-diphenylbut-1-ene, 1-p-(2,3-epoxypropoxy)phenyl-trans-1,2-diphenylbut-1-ene and 1-p-(2,3-dihydroxybutoxy)phenyl-trans-1,2-diphenylbut-1-ene.

A triphenylalkene derivative of the invention may be obtained by any process which is applicable to the manufacture of analogous compounds. A preferred process for its manufacture comprises the reaction of a triphenylalkene derivative of the formula:

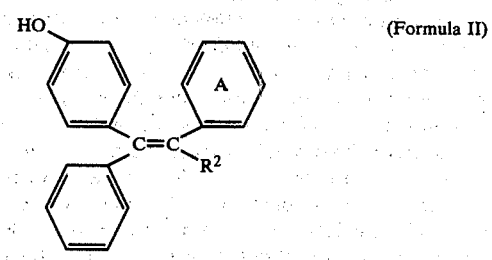

(Formula II)

wherein $R^2$ and A have the meanings stated above, with a compound of the formula $R^1$-X, wherein $R^1$ has the meaning stated above and X is a displaceable radical.

X may be, for example, a halogen or sulphonyloxy radical, for example the chloro, bromo, iodo, methanesulphonyoxy or p-toluenesulphonyloxy radical. The reaction is preferably carried out in the presence of a strong base, for example an alkali metal hydride or hydroxide, which forms the anion of the triphenylalkene starting material. The reaction is preferably carried out in a diluent or solvent, for example N,N-dimethylformamide.

Alternatively, the triphenylalkene derivative may be obtained by the dehydration of a compound of the formula:

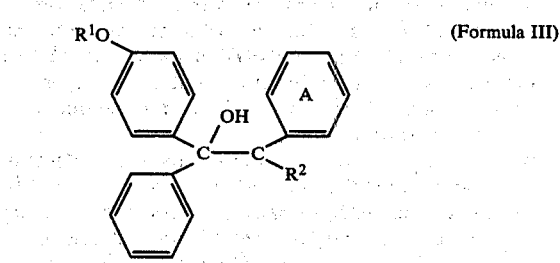

(Formula III)

wherein $R^1$, $R^2$ and A have the meanings stated above.

The dehydration is preferably carried out in the presence of an acid, for example hydrochloric acid, in a diluent or solvent, for example ethanol, at a temperature of from 20° to 80° C.

A triphenylalkene derivative of the invention wherein the substituent $R^1$ bears an oxygen atom may alternatively be obtained by different means. For example where the substituent $R^1$—O— has the partial structure.

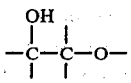

the compound may be obtained by the reaction of the triphenylalkene derivative of the formula (II) given above with the corresponding epoxy compound which has the partial structure

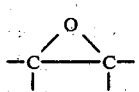

Alternatively a triphenylalkene derivative of the invention wherein the substituent $R^1$ bears two hydroxy substituents may be obtained by the oxidation with osmium tetroxide of the corresponding triphenylalkene derivative of the invention wherein the substituent $R^1$ contains an olefinic double bond, or by the base-catalysed hydrolysis of the corresponding triphenylalkene derivative of the invention wherein the substituent $R^1$ contains an epoxy substituent. A triphenylalkene derivative of the invention wherein the substituent $R^1$ bears one hydroxy substituent may be obtained by the hydroboronation of the corresponding triphenylalkene derivative of the invention wherein $R^1$ contains an olefinic double bond, or by the metal hydride reduction of the corresponding triphenylalkene derivative of the invention wherein the substituent $R^1$ contains an epoxy substituent.

The anti-oestrogenic activity of a triphenylalkene derivative of the invention has been demonstrated by its effect in preventing implantation of the fertilised ovum when administered orally to rats on day 4 of pregnancy. In this test, a preferred compound of the invention showed substantial activity at a dose of 0.2 mg./kg. and a particularly preferred compound showed activity at a dose of 0.01 mg./kg., this compound therefore being substantially more active than tamoxifen. Anti-oestrogenic activity can also be demonstrated by inhibition of the uterotrophic effect of an oestrogen in immature female rats.

A compound with the above pharmacological properties is of value in the treatment of the same conditions in which tamoxifen is beneficial, in particular, in the treatment of anovulatory infertility and in the treatment of breast tumours. It is also of value in the treatment of menstrual disorders.

When used to produce an anti-oestrogenic effect in warm blooded animals, a typical daily dose is from 0.05 to 1 mg./kg. administered orally or by injection. In man this is equivalent to an oral dose of from 5-80 mg./day. In use tamoxifen has been administered orally at doses of from 20-80 mg./day for the treatment of anovulatory infertility, and at doses from 10-40 mg./day for the treatment of breast tumours. A similar regime is appropriate for the administration of a triphenylalkene derivative of the invention, most conveniently in the form of a pharmaceutical composition.

According to a further feature of the invention, there is provided a pharmaceutical composition comprising a triphenylalkene derivative of the invention together with a pharmaceutically acceptable diluent or carrier.

The composition may be in a form suitable for oral or parenteral administration. A tablet or capsule is a particularly convenient form for oral administration, and such a composition may be made by conventional methods and contain conventional excipients. Thus a tablet could contain diluents, for example mannitol or maize starch, disintegrating agents, for example alginic acid, binding agents, for example methylcellulose, and lubricating agents, for example magnesium stearate.

The composition may contain, in addition to the triphenylalkene derivative of the invention, one or more antiandrogenic agents or antiprogestational agents.

A composition for oral administration may conveniently contain from 5-50 mg. of a triphenylalkene derivative of the invention, preferably 5-20 mg.

The invention is illustrated but not limited by the following Examples:

EXAMPLE 1

A solution of 1-p-hydroxyphenyl-trans-1,2-diphenylbut-1-ene (8.45 g.) in N,N-dimethylformamide (80 ml.) was added at laboratory temperature to a stirred suspension of sodium hydride (2.0 g. of a 50% dispersion in mineral oil from which the oil had been removed by washing with hexane) in N,N-dimethylformamide (15 ml.) under an atmosphere of argon. The mixture was stirred for 30 minutes, allyl bromide (3.2 ml.) was added and the mixture was stirred for a further 30 minutes and then poured into saturated aqueous ammonium chloride solution. The mixture was extracted three times with diethyl ether (100 ml. each time) and the combined extracts were washed five times with water (25 ml. each time), dried and evaporated to dryness. The residue was crystallised from ethanol and there was thus obtained 1-p-allyloxyphenyl-trans-1,2-diphenylbut-1-ene, m.p. 78.5°–79.5° C.

The 1-p-hydroxyphenyl-trans-1,2-diphenylbut-1-ene used as starting material was obtained as follows:

A 1.6 molar solution of methyl magnesium iodide in diethyl ether (45 ml.) was added to a solution of tamoxifen [1-p-(β-dimethylaminoethoxy)phenol-trans-1,2-diphenylbut-1-ene] (10.8 g.) in tetrahydrofuran (15 ml.) and the mixture was evaporated to dryness under reduced pressure at laboratory temperature. The residue was then heated in vacuo at a pressure of 1 mm. Hg. and at a temperature of 170°–200° C. for 1 hour, and then cooled to laboratory temperature. Diethyl ether (100 ml.) was added, then saturated aqueous sodium hydrogen tartrate solution (50 ml.) was carefully added, and then sufficient dilute aqueous hydrochloric acid was added to bring the solution to pH2. The ethereal layer was separated and the aqueous layer was washed twice with diethyl ether (50 ml. each time). The combined ethereal layers were dried and evaporated to dryness, and there was thus obtained as solid residue 1-p-hydroxyphenyl-trans-1,2-diphenylbut-1-ene, m.p. 129°–130° C.

EXAMPLE 2

The process described in Example 1 was repeated except that the appropriate halide was used in place of allyl bromide. There were thus obtained the compounds described in the following table:

(Formula IV)

$R^1O$—C₆H₄—C(=C(C₂H₅))—C₆H₅ (with additional phenyl)

| R¹ | m.p.(°C.) | crystallisation solvent | halide (R¹X) used | reaction conditions (temperature/time) |
|---|---|---|---|---|
| trans-but-2-enyl | 67 | ethanol | chloro | LT/2.5 hours |
| but-3-enyl | 76 | ethanol[1] | bromo | LT/24 hours |
| cyclohex-2-enyl | 93–94 | hexane[1] (at −20° C.) | bromo | LT/3 hours |
| trans-2,3-epoxybutyl | 101–103 | 10% diethyl ether in hexane. | chloro | 75–80° C./12 minutes |
| 2,3-epoxypropyl | 93–94.5 | 10% diethyl[2] ether in hexane | chloro | 70° C./0.5 hours |
| 2-methylthioethyl | 79–80 | hexane[3] (at −20° C.) | chloro | LT/3 hours then 70° C./3 hours |
| 1-methylprop-2-enyl | 100–101 | ethanol | chloro | 60° C./18 hours |
| 2-chloroprop-2-enyl | 80.5–81.5 | ethanol | chloro | LT/2 hours |
| 3-methylbut-2-enyl | 121–123 | ethanol | bromo | 70° C./5 hours |
| 3,4-epoxybutyl | 82 | 10% diethyl[3] ether in hexane. | bromo | LT/1 hour |

LT indicates laboratory temperature
Notes on crystallisation:-
Those compounds indicated were first purified by chromatography using the method described by Still et alia (J. Org. Chem., 1978, 43, 2923) with the following solvents systems:
[1] 1% diethyl ether in hexane
[2] 10% diethyl ether in hexane
[3] 1% ethyl acetate in toluene

EXAMPLE 3

The process described in Example 1 was repeated except that cyclohexene oxide (1,2-epoxycyclohexane) was used in place of allyl bromide, and the reaction was carried out at 80° C. for 18 hours. The product was purified by chromatography as described in Example 2 using 3% ethyl acetate in toluene as solvent system, and was then crystallised from ethanol. There was thus obtained 1-p-(2-hydroxycyclohexan-1-yloxy)phenyl-trans-1,2-diphenylbut-1-ene, m.p. 130°–131° C.

EXAMPLE 4

Osmium tetroxide (0.5 g.) was added to a solution of 1-p-allyloxyphenyl-trans-1,2-diphenylbut-1-ene (0.68 g.) in diethyl ether (20 ml.) and the mixture was stirred for 24 hours at laboratory temperature, treated with hydrogen sulphide and filtered. The filtrate was evaporated to dryness and the residue was crystallised from ether. There was thus obtained 1-(2,3-dihydroxypropoxy)phenyl-trans-1,2-diphenylbut-1-ene, m.p. 138°–139° C.

EXAMPLE 5

The process described in Example 4 was repeated except that the appropriate unsaturated triphenylalkene derivative was used as starting material in place of 1-p-allyloxyphenyl-trans-1,2-diphenylbut-1-ene. There were thus obtained the compounds of Formula IV described in the following table:

| R¹ | m.p. (°C.) | crystallisation solvent |
|---|---|---|
| 3,4-dihydroxybutyl | 99–101 | ether |
| 1-methyl-2,3-dihydroxypropyl (R,R) (S,S)- | 113–114 | isopropanol/hexane |
| 2,3-dihydroxybutyl | 99–100 | ether/hexane |
| cis-2,3-dihydroxycyclohexyl | 125 | ether/hexane |

EXAMPLE 6

Borane (0.7 ml. of an 0.6 molar solution in tetrahydrofuran) was added to a stirred solution of 1-p-allyloxyphenyl-trans-1,2-diphenylbut-1-ene (0.125 g.) in tetrahydrofuran (3 ml.) which was maintained at 0° C. under an atmosphere of argon. The mixture was stirred for 1 hour at 0° C., and then there was successively added water (2 ml.), aqueous N-sodium hydroxide solution (2 ml.) and aqueous 30% w/v hydrogen peroxide solution (1 ml.). The mixture was stirred for 30 minutes at 0° C., diluted with water (10 ml.) and extracted three times with diethyl ether (10 ml. each time). The combined extracts were washed successively with dilute aqueous sodium sulphite solution, aqueous sodium bicarbonate solution and saturated aqueous sodium chloride solution, and then dried and evaporated to dryness. The residue contained a mixture of two compounds having $R_f$ values 0.2 and 0.25 respectively when examined by thin layer chromatography on silica gel plates using a 5% v/v solution of ethyl acetate in toluene as developing solvent. The mixture was separated by preparative thin layer chromatography on silica gel plates using a 10% v/v solution of ethyl acetate in toluene as developing solvent and there were thus obtained 1-p-(3-hydroxypropoxy)phenyl-trans-1,2-diphenylbut-1-ene, m.p. 137° C. ($R_f$ 0.2) and 1-p-(2-hydroxypropoxy)phenyl-trans-1,2-diphenylbut-1-ene, m.p. 86.5°–87° C. ($R_f$ 0.25).

EXAMPLE 7

A solution of 1-p-(β-hydroxyethoxy)phenyl-1,2-diphenylbutan-1-ol (3.4 g.) in ethanol (50 ml.) was acidified with concentrated hydrochloric acid and heated under reflux for 3 hours. The ethanol was removed by evaporation and the residue was azeotroped with toluene and evaporated to dryness. The residue was triturated with petroleum ether (b.p. 40°–60° C.) and the solid residue was crystallised from petroleum ether (b.p. 80°–100° C.). There was thus obtained 1-p-(β-hydroxyethoxy)phenyl-trans-1,2-diphenylbut-1-ene, m.p. 103°–105° C.

The starting butanol was obtained as follows:

A solution of potassium hydroxide (2.8 g.) in a mixture of water (5 ml.) and ethanol (25 ml.) was added to a solution of 2-chloroethanol (24 g.) and 4-hydroxy-α-ethyldesoxybenzoin (12 g.) in ethanol (30 ml.). The mixture was stirred and heated under reflux for 10 hours, cooled and filtered. The filtrate was evaporated to dryness, the residue dissolved in water and the solution extracted 3 times with ether (100 ml. each time). The ethereal extract was washed with dilute aqueous sodium hydroxide solution, dried, evaporated to dryness and azeotroped with toluene. The toluene solution was evaporated to dryness and the residue triturated with petroleum ether b.p. 40°–60° C. There was thus obtained 1-p-(β-hydroxyethoxy)-α-ethyldesoxybenzoin, m.p. 72°–74° C.

A solution of the above compound (2.5 g.) in a mixture of ether (20 ml.) and tetrahydrofuran (2 ml.) was added to a stirred, cooled Grignard solution prepared from bromobenzene (8.2 g.), magnesium (1.26 g.) and ether (50 ml.). The mixture was then stirred and heated under reflux for 3 hours, cooled and a solution of ammonium chloride (10 g.) in water (50 ml.) was added dropwise. The ethereal layer was separated, the aqueous layer extracted twice with ether and the combined organic phases were dried and evaporated to dryness. There was thus obtained 1-p-(β-hydroxyethoxy)phenyl-1,2-diphenylbutan-1-ol as an oil which was used without further purification.

EXAMPLE 8

1-p-Allyloxyphenyl-1,2-diphenyl-butan-1-ol (26 g.) was dissolved in ethanol (150 ml.), concentrated hydrochloric acid (3 ml.) was added and the solution was heated under reflux for 3 hours. The reaction mixture was cooled to laboratory temperature, the ethanol was removed by evaporation and the residue was partitioned between hexane (250 ml.) and water (100 ml.). The hexane solution was separated, washed with saturated aqueous sodium bicarbonate solution (50 ml.), dried and evaporated to dryness. There was thus obtained a mixture of 1-p-allyloxyphenyl-trans-1,2-diphenylbut-1-ene and its cis isomer. The pure trans-isomer was obtained by crystallising the mixtue three times from ethanol.

The 1-p-allyloxyphenyl-1,2-diphenyl-butan-1-ol used as starting material was prepared as follows:

A solution of α-ethyldesoxybenzoin (14.7 g.) in dry tetrahydrofuran (20 ml.) was added to a stirred Grignard solution, heated under reflux under argon, prepared from magnesium (1.9 g.) and p-allyloxybromobenzene (16.8 g.) in dry tetrahydrofuran (20 ml.). The mixture was heated under reflux for 18 hours, cooled to laboratory temperature and poured into a saturated aqueous solution of ammonium chloride (250 ml.). The mixture was extracted three times with ether (50 ml. each time) and the combined ethereal extracts were dried and evaporated to dryness. There was thus obtained 1-p-allyloxyphenyl-1,2-diphenyl-butan-1-ol, m.p. 106°–106.5° C. after crystallisation from ethanol.

The process described in the first paragraph above was repeated using the appropriate 1-substitutedoxyphenyl-1,2-diphenylbutan-1-ol derivative as starting material. There were thus obtained the compounds of Formula I described in the following table (in all compounds $R^2$ is ethyl):

| $R^1$ | Ring A Substituent | m.p. (°C.) |
| --- | --- | --- |
| trans-but-2-enyl | 3-chloro | 91–92 |
| trans-but-2-enyl | 4-chloro | 85 |
| but-3-enyl | 3-chloro | 109–110 |
| but-3-enyl | 4-chloro | 85–86 |
| but-3-enyl | 4-methoxy | 89–91 |

The butanol starting materials were prepared by a similar process to that described in the second paragraph above from the approrpriate α-ethyldesoxybenzoin and the Grignard reagent prepared from either p-(trans-but-2-enyloxy)bromobenzene (b.p. 96° C.@0.4 mm.Hg.) or p-but-3-enyloxybromobenzene (b.p. 120° C.@0.1 mm Hg.), the bromobenzene derivatives themselves being prepared from p-bromophenol and either 1-chloro-trans-but-2-ene or 1-bromobut-3-ene in boiling acetone in the presence of potassium carbonate.

EXAMPLE 9

The process described in Example 4 was repeated except that the appropriate unsaturated triphenylalkene derivative was used as starting material in place of 1-p-allyloxyphenyl-trans-1,2-diphenylbut-1-ene. There were thus obtained the compounds of Formula I described in the following table (in all compounds $R^2$ is ethyl):

| $R^1$ | Ring A Substituent | m.p. (°C.) |
| --- | --- | --- |
| 3-methyl-2,3-dihydroxybutyl | — | 112–114 |
| 3,4-dihydroxybutyl | 3-chloro | (oil) $R_F$ 0.37* |
| 3,4-dihydroxybutyl | 4-chloro | (oil) $R_F$ 0.32* |
| 3,4-dihydroxybutyl | 4-methoxy | (oil) $R_F$ 0.32* |

*$R_F$ values on thin-layer silica chromatography plates using a 5% v/v solution of methanol in methylene dichloride as developing solvent.

EXAMPLE 10

The process described in Example 1 was repeated except that 1-p-hydroxyphenyl-cis-1,2-diphenylbut-1-ene (prepared from the cis-isomer of tamoxifen by a similar process to that described in the second part of Example 1) and trans-but-2-enyl chloride are used as starting materials. There was thus obtained 1-p-(trans-but-2-enyloxy)phenyl-cis-1,2-diphenylbut-1-ene, m.p. 87° C.

EXAMPLE 11

The process described in Example 4 was repeated except that the cis-but-1-ene described in Example 10 was used as starting material. There was thus obtained 1-p-[(R,R)(S,S)-2,3-dihydroxybutoxy]phenyl-cis-1,2-diphenylbut-1-ene, m.p. 113°–114° C.

EXAMPLE 12

A solution of potassium hydroxide (0.45 g.) in water (3 ml.) was added to a solution of 1-p-(trans-2,3-epoxybutoxy)phenyl-trans-1,2-diphenylbut-1-ene (0.167 g.) in dimethylsulphoxide (8 ml.) and the mixture was heated at 100° C. for 3.5 hours, cooled and poured into water (50 ml.). The mixture was extracted three times with diethyl ether (10 ml. each time) and the combined ethereal extracts were dried over anhydrous sodium sulphate and evaporated to dryness. The residue was purified by chromatography by the method of Still et alia described in Example 2, using diethyl ether as eluant, and the appropriate fractions were combined and evaporated to dryness. The residue was crystallised from a 1:1 v/v mixture of diethyl ether and hexane and there was thus obtained 1-p-[(R,S)(S,R)-2,3-dihydroxybutoxy]phenyl-trans1,2-diphenylbut-1-ene, m.p. 98°–100° C.

EXAMPLE 13

1,2-dibromoethane (4.3 ml.) was added to a solution of 1-p-hydroxyphenyl-trans-1,2-diphenylbut-1-ene (3 g.) and potassium hydroxide (0.56 g.) in ethanol (12 ml.) and water (2 ml.) and the mixture was stirred and heated under reflux for 4 hours, cooled and filtered. The filtrate was evaporated to dryness and the solid residue was extracted twice and diethyl ether (50 ml. each time). The combined ethereal extracts were washed with aqueous 2 N-sodium hydroxide solution and then with water, dried over anhydrous sodium sulphate and evaporated to dryness. The residue was purified by chromatography by the method of Still et alia described in Example 2, using toluene as eluant, and the appropriate fractions were combined and evaporated to dryness. The residue was crystallised from hexane and there was thus obtained 1-p-(2-bromoethoxy)phenyl-trans-1,2-diphenylbut1-ene, m.p. 106°–107° C. Sodium methoxide (4 equivalents) was added to a solution of the above compound (0.1 g.) in dry methanol and the mixture was heated under reflux for 7 hours and then cooled and concentrated. The concentrated solution was subject to preparative layer chromatography on silica gel plates using toluene as eluant. The material with $R_F$ 0.8 on thin-layer silica plates using a 1:1 v/v mixture of ethyl acetate and toluene as developing solvent was eluted from the preparative plates with ethyl acetate, and the solution was evaporated. The residue, which crystallised slowly, was 1-p-(2-methoxyethoxy)phenyl-trans-1,2-diphenylbut-1-ene, m.p. 74° C.

What we claim is:

1. A triphenylalkene derivative of the formula:

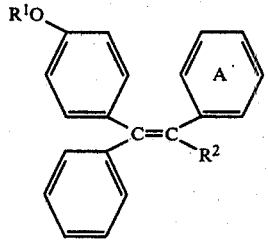

(Formula I)

wherein $R^1$ is alkenyl, cycloalkenyl, cycloalkenylalkyl, halogenoalkenyl, hydroxyalkyl, dihydroxyalkyl, hydroxycycloalkyl, dihydroxycycloalkyl, hydroxycycloalkylalkyl or epoxyalkyl, wherein $R^2$ is alkyl of up to 6 carbon atoms, halogen or nitro and wherein ring A may optionally bear a halogen substituent or an alkoxy substituent of up to 4 carbon atoms.

2. A triphenylalkene derivative as claimed in claim 1 which has the trans-configuration, wherein $R^1$ is alkenyl, dihydroxyalkyl or epoxyalkyl each of 3 or 4 carbon atoms, wherein $R^2$ is alkyl of up to 6 carbon atoms and wherein ring A bears no further substituent.

3. A triphenylalkene derivative as claimd in claim 2 wherein $R^2$ is ethyl.

4. The compound 1-p-allyloxyphenyl-trans-1,2-diphenyl-but-1-ene, 1-p-(2,3-dihydroxypropoxy)phenyl-trans-1,2-diphenyl-but-1-ene, 1-p-(2,3-epoxypropoxy)phenyl-trans-1,2-diphenylbut-1-ene or 1-p-(2,3-dihydroxybutoxy)phenyl-trans-1,2-diphenylbut-1ene.

5. A compound according to claim 1, said compound being 1-p-allyloxyphenyl-trans-1,2-diphenyl-but-1-ene.

6. A pharmaceutical composition having antioestrogenic activity which comprises a triphenylalkene derivative, claimed in claim 1, together with a pharmaceutically-acceptable diluent or carrier.

7. A method for producing an antioestrogenic effect in a warm-blooded animal which comprises administering to said animal an effective amount of a triphenylalkene derivative claimed in claim 1.

* * * * *